(12) United States Patent
O'Brien

(10) Patent No.: US 7,972,338 B2
(45) Date of Patent: Jul. 5, 2011

(54) SELF-SUPPORTING OSTEOTOMY GUIDE AND RETRACTION DEVICE AND METHOD OF USE

(76) Inventor: Todd O'Brien, West Enfield, ME (US)

( * ) Notice: Subject to any disclaimer, the term of this patent is extended or adjusted under 35 U.S.C. 154(b) by 1077 days.

(21) Appl. No.: 11/752,366

(22) Filed: May 23, 2007

(65) Prior Publication Data
US 2008/0294170 A1 Nov. 27, 2008

(51) Int. Cl.
*A61F 5/00* (2006.01)
(52) U.S. Cl. .......................................................... 606/87
(58) Field of Classification Search ..................... 606/87
See application file for complete search history.

(56) References Cited

U.S. PATENT DOCUMENTS

| 4,627,425 | A | 12/1986 | Reese |
| 5,147,365 | A | 9/1992 | Whitlock et al. |
| 5,601,565 | A | 2/1997 | Huebner |
| 5,613,969 | A | 3/1997 | Jenkins, Jr. |
| 5,645,548 | A | 7/1997 | Augsburger |
| H1706 | H | 1/1998 | Mason |
| 5,722,978 | A | 3/1998 | Jenkins, Jr. |
| 5,843,085 | A | 12/1998 | Graser |
| 5,980,526 | A | 11/1999 | Johnson et al. |
| 6,391,031 | B1 | 5/2002 | Toomey |
| 6,605,088 | B1 | 8/2003 | St. Onge et al. |

*Primary Examiner* — Thomas C Barrett
*Assistant Examiner* — Sameh Boles
(74) *Attorney, Agent, or Firm* — Anthony D. Pellegrini, Esq.

(57) ABSTRACT

An improved osteotomy guide and retraction device for use during the performance of bunionectomies, whereby the improved device provides a self-supporting instrument that does not require independent fastening means to secure the device in the desired position at the surgical site, and a method of use of the device.

18 Claims, 4 Drawing Sheets

SELF-SUPPORTING OSTEOTOMY GUIDE AND RETRACTION DEVICE AND METHOD OF USE

BACKGROUND OF THE INVENTION

1. Technical Field

The invention relates generally to the field of surgical instruments. More specifically, the invention is directed to an improved osteotomy guide and retraction device to be used during the performance of bunionectomies to provide a self-supporting instrument that does not require independent fastening means to the surgical site. It is also directed to a method of use of the device.

2. Description of Prior Art

It has been estimated that 170,000 bunionectomies are performed annually in the United States. The chevron osteotomy, in which two linear incisions are made through the head of the metatarsal, with the two incisions intersecting to form a v-shaped acute angle between the incisions, is one of the most commonly performed bunionectomy procedures, widely used by orthopedic and podiatric surgeons.

Osteotomy guides, in general, are utilized in order to improve the accuracy and reproducibility of orthopedic procedures. This is accomplished by guiding the surgeon's hand during the creation of osteotomies with a surgical saw. This technique is much like industrial processes where a template is used when cutting wood or metal. Various orientations are integrated into the guides for specific procedures. Current trends in orthopedics favor such devices as a method of reducing variation in technique. The superior osteotomies created by these devices result in enhanced bone healing and more predictable results. They are particularly valuable in reconstructive and joint replacement procedures.

There are various styles of osteotomy guides known in the art. These typically are planar and constructed of a metal material, and have formed into them two or more slots, usually describing a chevron cut. These guides are placed against and secured to the metatarsal in the appropriate position, then a surgical saw blade is passed through the slots and into and through the bone, forming the desired incisions. While this has proven to be a simple yet effective means for accurately performing an osteotomy, these guides suffer the deficiency of requiring additional instruments to secure them to the surgical site. The most common means for securing these devices is by use of Kirschner wires, or "K-wires". The K-wires are inserted through small apertures formed in the osteotomy guide and embedded into the underlying bone.

In addition to needing further instruments to secure prior art osteotomy guides to the bone, the surgeon also typically employs a number of retractors to move soft tissues away from the surgical site. This often leads to bunionectomies requiring not only a surgeon but also a first assistant, to manipulate the retractors.

From the foregoing, it is evident that there is a need for an improved osteotomy guide device to be used during the performance of bunionectomies, where such a device is self-supporting at the surgical site and further provides retraction capabilities, thereby reducing the number of independent instruments required to perform the procedure and eliminating the need for surgical assistants.

It is therefore an objective of the present invention to provide an improved osteotomy guide device to be used during the performance of bunionectomies.

It is a further objective of the present invention to provide an improved osteotomy guide device which is self-supporting at the surgical site without need of additional independent fastening devices.

It is yet a further objective of the present invention to provide an improved osteotomy guide device which provides retraction capabilities.

It is yet a still further objective of the present invention to provide an improved osteotomy guide device which simplifies bunionectomy procedures.

It is yet a still further objective of the present invention to provide a method of using the improved osteotomy guide device of the present invention in a bunionectomy procedure.

Other objectives of the present invention will be readily apparent from the description that follows.

SUMMARY OF THE INVENTION

The invention comprises an osteotomy guide and retraction device for use in bunionectomy procedures and a method of use of same. The device is used to guide a cutting blade into and through the head of the metatarsal bone of the human foot, the incisions being made in at least two adjacent locations, for the purpose of thereafter allowing the remaining bone to be properly repositioned and fixated. The device improves upon prior art used for this same function by being self-supporting at the surgical site; that is, by being adapted to clamp onto the neck of the metatarsal and to lock in place. This obviates the need for independent fastening means, such as K-wires, to hold the osteotomy guide in place. The device also provides retraction capabilities, whereby certain tendons and other soft tissues are positioned away from the cutting blade and otherwise protected from injury. Having a single device provide the osteotomy guide as well as retraction capabilities reduces the number of independent retractors needed for the procedure and allows bunionectomies to be performed without assistance.

The present invention comprises a guide plate having two or more guide slots, a primary metatarsal engagement device suitably adapted to engage the guide plate with the neck of the metatarsal, a locking hinged clamp having two jaws and a handle and integrated with the guide plate, and a secondary metatarsal engagement device integrated with the clamp and suitably adapted to engage with the neck of the metatarsal to provide counter pressure opposite the guide plate, thereby serving to secure the guide plate in place when the clamp is locked. The primary metatarsal engagement device depends from the primary jaw of the clamp and the secondary metatarsal engagement device depends from the secondary jaw of the clamp. The primary and secondary metatarsal engagement devices are moved towards and away from each other by manual manipulation of the handle portion of the clamp. The locking assembly of the clamp retains the primary and secondary metatarsal engagement devices in fixed position relative to each other during use of the device, resulting in the guide plate being securely positioned.

The above configuration aligns the guide slots of the guide plate over the head of the metatarsal during use, such that properly positioned incisions may be made through the head of the metatarsal using a surgical saw, such as a sagital saw. It also enables the clamp jaws to provide retraction capabilities to certain tendons and soft tissue when the device is properly positioned. Specifically, the secondary jaw of the clamp is adapted to displace the extensor tendon and retain it away from the cutting blade.

The device of the present invention may be configured for either right- or left-handed use.

The method of use of the device of the present invention involves the steps of preparing the surgical site of the bunionectomy by dissecting the soft tissues to expose the metatarsal and performing an exostectomy of a portion of the metatarsal, using standard technique; positioning the device onto the metatarsal at the site of the exostectomy and fixing its position thereto; retracting soft tissues away from the device; making two or more incisions into and through the head of the metatarsal using the guide slots of the guide plate to ensure properly positioned incisions; removing the device; then manipulating the remaining portions of the metatarsal into the desired position, fixating the metatarsal by the use of fasteners to retain it in the desired position, and closing the surgical site, using standard technique.

Other features and advantages of the invention are described below.

Figure 2:
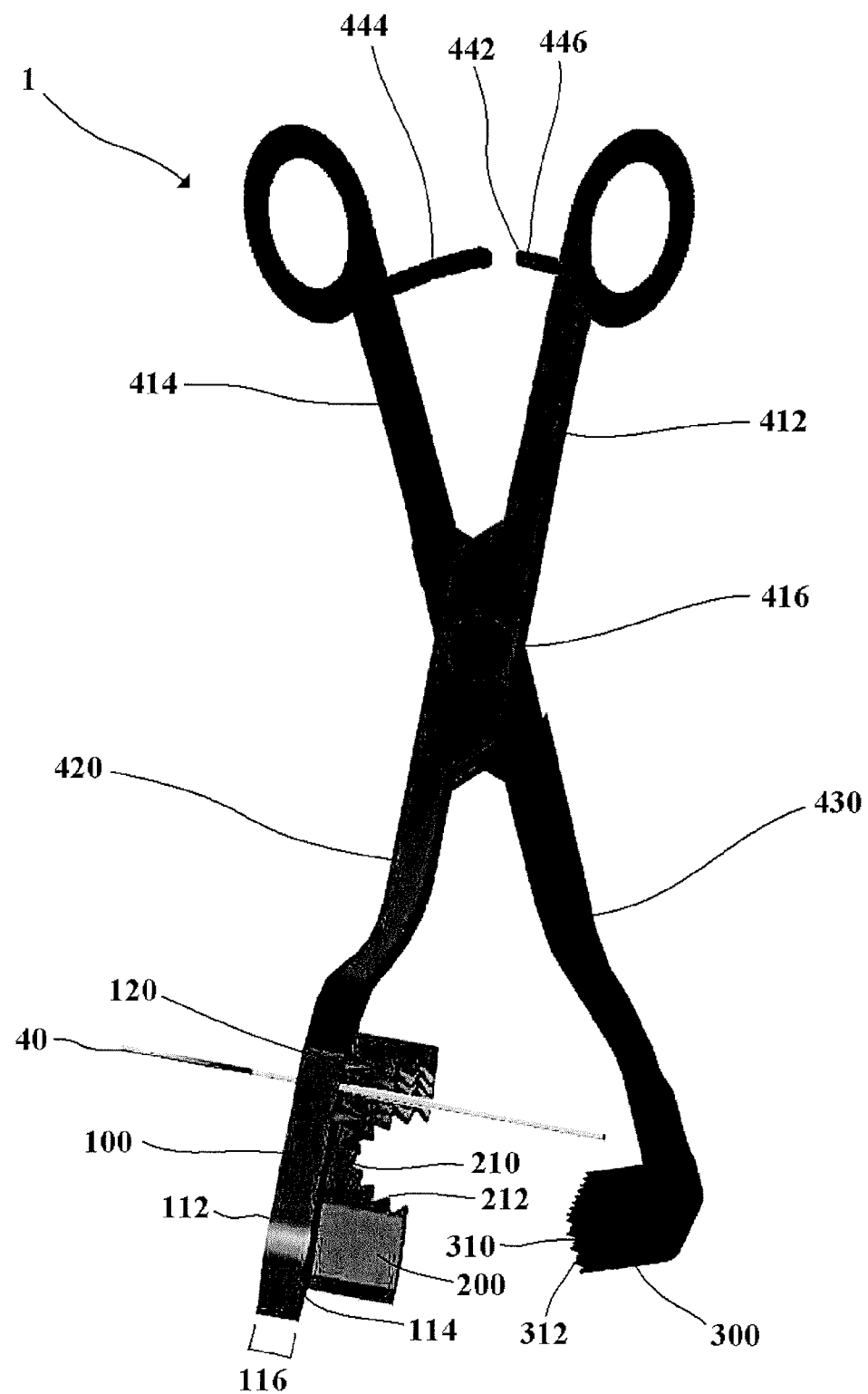
FIG. 2 is a front perspective view of the present invention depicting the clamping member in an open position, with a cutting blade inserted into and through a guide slot.

DETAILED DESCRIPTION OF THE INVENTION:

The present invention is an improved osteotomy guide and retraction device 1 to be used by a surgeon during a bunionectomy procedure. See FIG. 2. The device 1 is suitably adapted to be removably attached to the neck 14 of a metatarsal bone 10 to guide a cutting blade 40 into and through the head 12 of the metatarsal 10 as part of the bunionectomy procedure.

The device 1 comprises four principle components: a guide plate 100, a primary metatarsal engagement device 200, a secondary metatarsal engagement device 300, and a clamp 400. See FIG. 2. These components are integrated with each other, with the guide plate 100 and the secondary metatarsal engagement device 300 depending from the clamp 400 and the primary metatarsal engagement device 200 depending from the guide plate 100. The clamp 400 is suitably adapted to position the primary metatarsal engagement device 200 and the secondary metatarsal engagement device 300 toward and away from each other and is further suitably adapted to lock the primary metatarsal engagement device 200 and the secondary metatarsal engagement device 300 into a fixed position relative to each other. In the preferred embodiment, the guide plate 100, the primary metatarsal engagement device 200, the secondary metatarsal engagement device 300, and the clamp 400 are constructed of surgical stainless steel.

Figure 1:
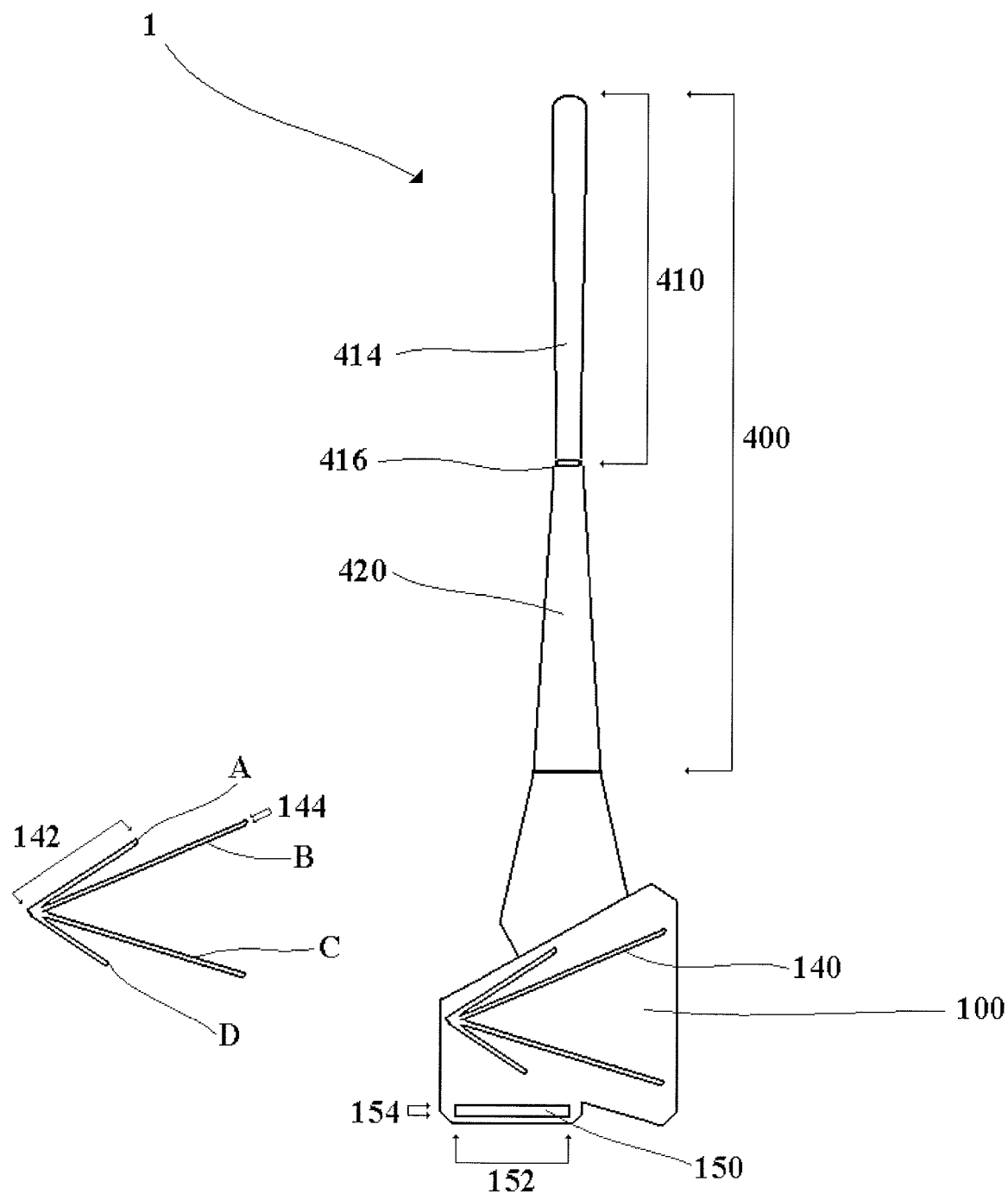
FIG. 1 is a side plan view of the present invention depicting the guide plate configured with four guide slots, with said guide slots also shown in greater detail.

The guide plate 100 is substantially planar and has an outer surface 112, an inner surface 114, and a thickness 116. See FIG. 2. It is placed against the metatarsal 10, with the inner surface 114 of the guide plate 100 positioned adjacent to the metatarsal 10 during use. The guide plate 100 comprises two or more guide slots 140. See FIG. 1. Each guide slot 140 is substantially linear and is formed into and passes completely through the thickness 116 of the guide plate 100. Each guide slot 140 has a length 142 and a width 144. The width 144 of each guide slot 140 is slightly wider than the thickness of a cutting blade 40, such that the cutting blade 40 may be passed into and through the guide slot 140. In the preferred embodiment the width 144 of the guide slots 140 is between 0.45 mm and 0.55 mm, to accommodate a standard 0.4 mm cutting blade 40. The length 142 of each guide slot 140 is greater that the width of the cutting blade 40, and is of a sufficient length to permit the cutting blade 40 to move along the length 142 of the guide slot 140 to make an appropriate length incision into and through the head 14 of the metatarsal 10. The thickness 116 of the guide plate 100 must be sufficient to provide the guide plate 100 with necessary rigidity and also to provide a sufficient depth to each guide slot 140 to minimize pivoting of the cutting blade 40 when making an incision into and through the head 14 of the metatarsal 10. In the preferred embodiment the thickness 116 of the guide plate 100 is between 3.5 mm and 4.5 mm, with the most preferred thickness 116 of the guide plate 100 being 4.0 mm.

The guide slots 140 are oriented with respect to each other in a suitable configuration to delineate the desired positions of the incisions into and through the head 12 of the metatarsal 10. In one embodiment of the device 1 having two guide slots 140, the guide slots 140 are oriented at an acute angle to each other, with one end of each guide slot 140 intersecting one end of the other guide slot 140. This configuration delineates a chevron cut. Typically, for chevron cuts, the acute angle formed between the two guide slots 140 is between 50 degrees and 60 degrees. In another embodiment of the device 1 having two guide slots 140, the guide slots 140 are oriented at a substantially 90 degree angle to each other, to create a so-called "L-cut". In another embodiment the two guide slots 140 are oriented substantially parallel to each other. In an embodiment of the device 1 having three guide slots 140, two of the guide slots 140 are oriented substantially parallel to each other with the third guide slot 140 forming a diagonal connecting opposing ends of the parallel guide slots 140, to create a so-called "Z-cut".

In the preferred embodiment of the device 1, the guide plate 100 comprises four guide slots 140. The four guide slots 140 are denoted A, B, C, and D, respectively, with all four guide slots 140 intersecting with each other at an end, forming acute angles. See FIG. 1. Guide slot A forms a substantially 60 degree angle with guide slot D and guide slot B forms a substantially 40 degree angle with guide slot C. Guide slot A forms a substantially 10 degree angle with guide slot B and guide slot C forms a substantially 10 degree angle with guide slot D. Finally, guide slot A forms a substantially 50 degree angle with guide slot C and guide slot B forms a substantially 50 degree angle with guide slot D. So configured, four different chevron cuts may be made with a single device 1, of 60 degrees, 40 degrees, and two of 50 degrees. Additionally, guide slot B and guide slot C are longer than guide slot A and guide slot D. In one configuration guide slot A and guide slot D are between 1.5 cm and 2.0 cm long each, with a preferred length of 1.7 cm each, and guide slot B and guide'slot C are between 2.5 cm and 3.0 cm long each, with a preferred length of 2.7 cm each. The foregoing allows the surgeon to accommodate variations in the anatomy of different metatarsals 10 by facilitating the making of multiply configured chevron cuts into and through the head 12 of the metatarsal 10. Every other useful configuration of guide slots 140 is also contemplated by the present invention.

In one embodiment the guide plate 100 comprises one or more bone engagement members 120. See FIG. 2. Each bone engagement member 120 depends substantially perpendicularly from the inner surface 114 of the guide plate 100. Each bone engagement member 120 is suitably adapted to engage with the metatarsal 10, thereby assisting in securing the guide plate 100 to the metatarsal 10 and minimizing lateral slippage, so that the guide plate 100 remains correctly positioned with respect to the head 12 of the metatarsal 10. The bone engagement members 120 may be configured as spikes, or teeth, or sharpened wedges, or any other suitable configuration.

Figure 3:
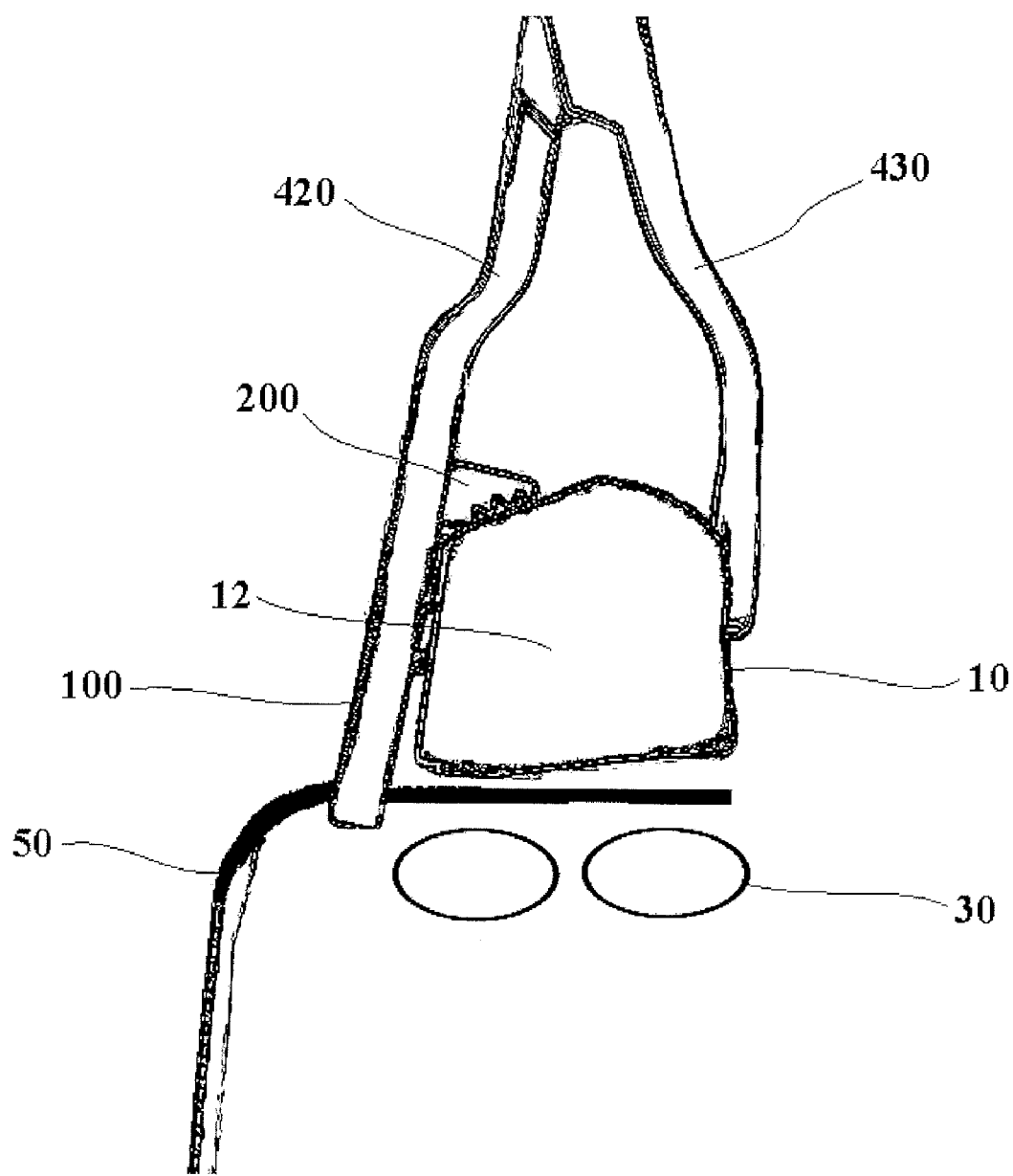
FIG. 3 is a cut-away front plan view of the present invention and a portion of the metatarsal, depicting the present invention engaged with the metatarsal behind the head of the metatarsal, with a malleable retractor inserted into and through the retractor slot with a portion of same interposed between the metatarsal and the sesamoid bones.
Figure 4:
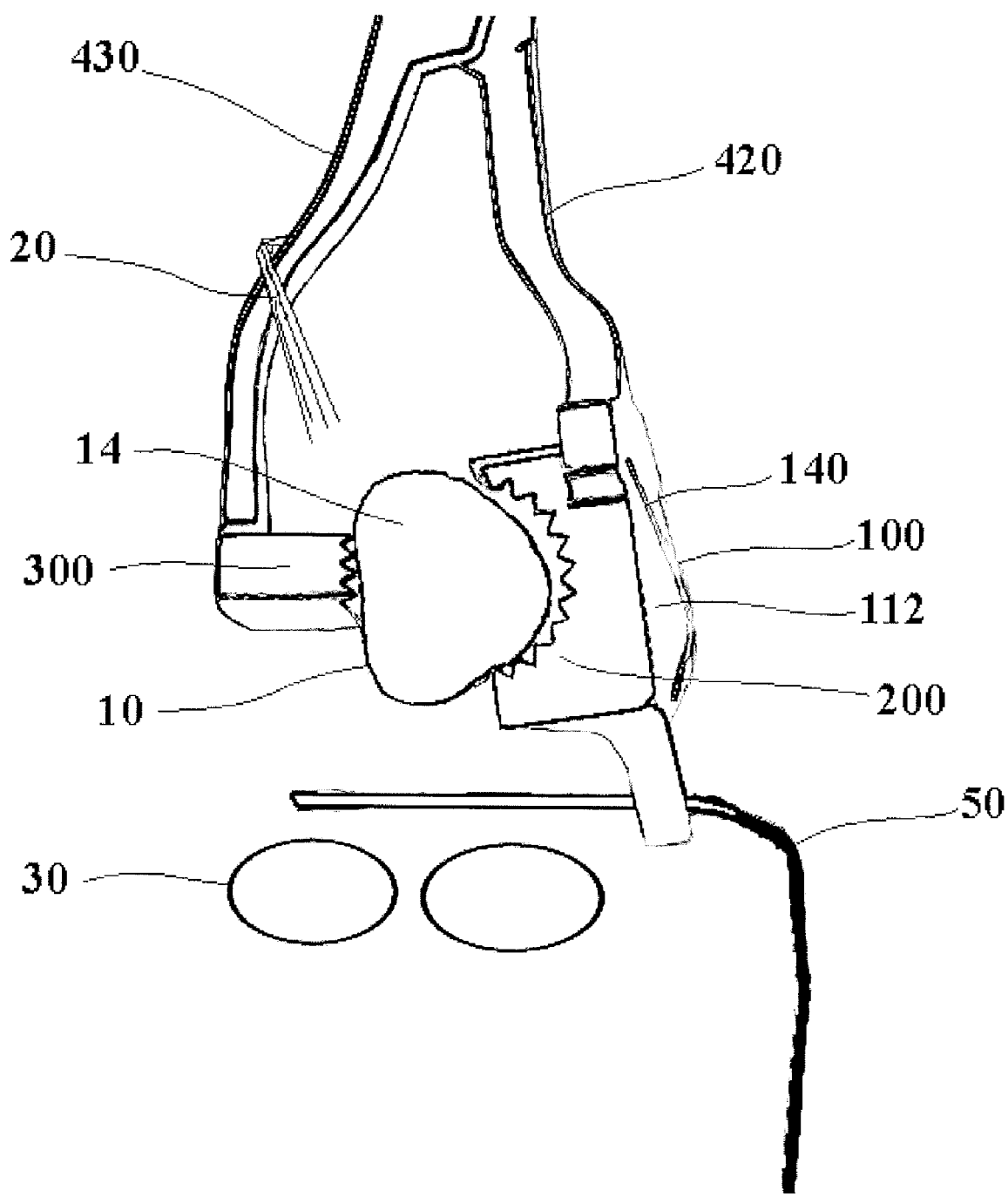
FIG. 4 is a cut-away rear perspective view of the present invention and a portion of the metatarsal, depicting the present invention engaged with the neck of the metatarsal, with a malleable retractor inserted into and through the retractor slot with a portion of same interposed between the metatarsal and the sesamoid bones, and with a tendon retracted against the secondary jaw.

In another embodiment the guide plate 100 further comprises a retractor slot 150. See FIG. 1. The retractor slot 150 is suitably adapted to accommodate a malleable retractor 50. The retractor slot 150 is substantially linear and is formed into and passes completely through the thickness 116 of the guide plate 100. The width 154 of the retractor slot 150 is slightly wider than the thickness of the malleable retractor 50, and the length 152 of the retractor slot 150 is slightly longer than the width of the malleable retractor 50. In the preferred embodiment the width 154 of the retractor slot 150 is between 2.5 mm and 3.5 mm, with the preferred width being 3.0 mm, to accommodate the thickness of a standard malleable retractor 50, and the length 152 of the retractor slot 150 is between 1.0 cm and 2.0 cm, with the preferred length being 1.5 cm, to accommodate the width of a standard malleable retractor 50. An end of the malleable retractor 50 is passed into and through the retractor slot 150 so that at least a portion of the malleable retractor 50 extends below the head 12 of the metatarsal 10 and is interposed between the head 12 of the metatarsal 10 and the sesamoid bones 30, thereby protecting the sesamoid bones 30 from the cutting blade 40. See FIGS. 3 and 4. The opposite end of the malleable retractor 50 may then be positioned downward to retract soft tissues away from the guide plate 100 and the cutting blade 40. Utilizing a malleable retractor 50 inserted into and through the retractor slot 150 eliminates the need for a separately held retractor.

The primary metatarsal engagement device 200 is located on the inner surface 114 of the guide plate 100 and is suitably adapted to correctly position the guide plate 100 with respect to the head 12 of the metatarsal 10. See FIG. 2. That is, the location of the primary metatarsal engagement device 200 on the inner surface 114 of the guide plate 110 is such that when the primary metatarsal engagement device 200 is aligned with the neck 14 of the metatarsal 10 the guide slots 140 are properly aligned with the head 12 of the metatarsal 10. See FIG. 4. The primary metatarsal engagement device 200 has an open, substantially concave configuration forming an engagement surface 210 suitably adapted to snugly fit over and against a portion of the neck 14 of the metatarsal 10. The concavity of the primary metatarsal engagement device 200 may be substantially cylindrical, or it may be elliptical, or it may have an irregular curvature to more closely approximate the curvature of the neck 14 of the metatarsal. The primary metatarsal engagement device 200 may be fixedly attached to the guide plate 100, for example, with spot welds, or may be more fully integrated with the guide plate 100. In the preferred embodiment the primary metatarsal engagement device 200 and the guide plate 100 are formed of a unitary piece of metal.

In one embodiment the engagement surface 210 of the primary metatarsal engagement device 200 comprises a plurality of gripping members 212. See FIG. 2. Each gripping member 212 may be configured as a spike, or a tooth, or a sharpened wedge, or any other suitable configuration. The gripping members 212 are suitably adapted to prevent the primary metatarsal engagement device 200 from rotating about or slipping along the neck 14 of the metatarsal 10. In the preferred embodiment the gripping members 212 cover substantially all of the engagement surface 210 of the primary metatarsal engagement device 200.

In another embodiment of the present invention at least one guide slot 140 is formed into and passes completely through the primary metatarsal engagement device 200. This configuration allows the guide plate 100 to be more compact, while still accommodating full length guide slots 140. In the preferred embodiment having four guide slots 140, as described above, guide slot C is formed into and passes completely through the primary metatarsal engagement device 200.

The secondary metatarsal engagement device 300 is suitably adapted to provide counter pressure to the primary metatarsal engagement device 200. The secondary metatarsal engagement device 300 is suitably adapted to engage with the neck 14 of the metatarsal 10 on the side of the neck 14 of the metatarsal 10 opposite where the primary metatarsal engagement device 200 is engaged with the neck 14 of the metatarsal 10. See FIG. 4. The secondary metatarsal engagement device 300 has an engagement surface 310 suitably adapted to engage the neck 14 of the metatarsal 10. See FIG. 2. In one embodiment the secondary metatarsal engagement device 300 is substantially cubical, providing an engagement surface 310 which is substantially planar. In another embodiment, the secondary metatarsal engagement device 300 has an open, substantially concave configuration suitably adapted to fit over the neck 14 of the metatarsal 10. In this configuration the engagement surface 310 is substantially curved. The engagement surface 310 of the secondary metatarsal engagement device 300 may also comprise a plurality of gripping members 312. These gripping members 312 may be configured substantially the same as and serve the same purpose as the gripping members 212 of the primary metatarsal engagement device 200. In the preferred embodiment the gripping members 312 of the secondary metatarsal engagement device 300 cover substantially all of the engagement surface 310 of the secondary metatarsal engagement device 300.

In another embodiment of the present invention the engagement surface 310 of the secondary metatarsal engagement device 300 is oriented at an angle to the inner surface 114 of the guide plate 100 to better accommodate the anatomy of the head 12 of the metatarsal 10. In the preferred embodiment the angle of the engagement surface 310 of the secondary metatarsal engagement device 300 relative to the inner surface 114 of the guide plate 100 is between 6 degrees and 10 degrees, with the most preferred embodiment having an angulation of 8 degrees.

The clamp 400 comprises a handle assembly 410, a primary jaw 420, a secondary jaw 430, and a locking assembly 440. See FIG. 2. The clamp 400 is integrated with the guide plate 100 and the secondary metatarsal engagement device 300, with the guide plate 100 depending from the primary jaw 420 of the clamp 400 and the secondary metatarsal engagement device 300 depending from the secondary jaw 430 of the clamp 400. Manipulation of the clamp 400 positions the primary metatarsal engagement device 200 and the secondary metatarsal engagement device 300 towards and away from each other.

The handle assembly 410 of the clamp 400 has a first handle 412, a second handle 414, and a hinge mechanism 416. The first and second handles 412,414 are suitably adapted to be held and manipulated by a human hand and to articulate about the hinge mechanism 416. Manipulation of the first and second handles 412,414 causes the primary and secondary jaws 420,430 to move towards and away from each other. This is a standard configuration found in many hinged hand-held instruments, such as forceps, scissors, and the like.

The primary jaw 420 of the clamp 400 depends from the first handle 412, with the hinge mechanism 416 interposed between the primary jaw 420 and the first handle 412. The secondary jaw 430 of the clamp 400 depends from the second handle 414, with the hinge mechanism 416 interposed between the secondary jaw 430 and the second handle 414. The guide plate 100 is integrated with and depends from the primary jaw 420, and the secondary metatarsal engagement device 300 is integrated with and depends from the secondary jaw 430. In one embodiment the first handle 412, the primary jaw 420, the guide plate 100, and the primary metatarsal engagement device 200 are formed of a unitary piece of metal, and the second handle 414, the secondary jaw 430, and the secondary metatarsal engagement device 300 are formed of a unitary piece of metal.

The secondary jaw 430 is suitably adapted to provide retraction of an extensor tendon 20. The secondary jaw 430 displaces the tendon 20 away from the head 12 of the metatarsal 10 and retains the tendon 20 in a retracted position while the device 1 is engaged upon the neck 14 of the metatarsal 10. See FIG. 4. The secondary jaw 430 may be appropriately curved to securely retract the tendon 20 during use while minimizing slippage.

The locking assembly 440 is integrated with the handle assembly 410. The locking assembly 440, when in a locked state, is suitably adapted to hold the primary and secondary jaws 420,430 in a fixed position relative to each other. When the locking assembly 440 is in an unlocked state the primary and secondary jaws 420,430 may move relative to each other. The locking assembly 440 may be of any suitable configuration to perform this function. In one embodiment the locking assembly 440 comprises a first toothed arm 442 and a second toothed arm 444. The first toothed arm 442 has a plurality of teeth 446 and the second toothed arm 444 has a plurality of teeth 446. The first toothed arm 442 depends from the first handle 412 in a substantially perpendicular orientation, and the second toothed arm 444 depends from the second handle 414 in a substantially perpendicular orientation, substantially overlapping the first toothed arm 442. The teeth 446 of the first toothed arm 442 are oriented towards the teeth 446 of the second toothed arm 444 so that when the first and second handles 412,414 are manipulated the teeth 446 of the first toothed arm 442 slide along and engage with the teeth 446 of the second toothed arm 444. Other clamp locking assemblies are well known in the field of surgical instruments and are contemplated by the present invention.

The present invention is also directed to a method of use of the device 1 in performing a bunionectomy on a metatarsal bone 10. The method comprises the following steps:

1. preparing a patient for surgery using standard technique;
2. exposing the head 12 and neck 14 of the metatarsal 10 medially, dorsally, and laterally, using standard technique;
3. performing an exostectomy of the metatarsal head 12 using standard technique;
4. retracting the extensor tendon 20 away from the site of the exostectomy;
5. positioning the device 1 onto the exposed metatarsal neck 14 and against the metatarsal head 12 by engaging the primary metatarsal engagement device 200 with the metatarsal neck 14, engaging the secondary metatarsal engagement device 300 with the metatarsal neck 14 opposite the primary metatarsal engagement device 200, and locking the device 1 into position;
6. positioning the extensor tendon 20 against the secondary jaw 430 of the device 1 such that the tendon 20 is retracted by the secondary jaw 430, whereby the secondary jaw 430 is interposed between the tendon 20 and the metatarsal 10;
7. making two or more incisions into and through the metatarsal head 12 with a cutting blade 40, by inserting the cutting blade 40 into and through two or more guide slots 140 of the device 1 and continuing to move the cutting blade 40 into and through the metatarsal head 12;
8. removing the device 1 from the metatarsal 10;
9. manipulating the metatarsal 10 into the desired position using standard technique;
10. fixating the metatarsal 10 using standard technique; and
11. closing the soft tissues using standard technique.

When an embodiment of the device 1 having a retractor slot 150 formed into the guide plate 100 is used, the method may be modified by employing the following additional step:

6A. positioning an end of a malleable retractor 50 into and through the retractor slot 150 of the guide plate 100, such that at least a portion of the malleable retractor 50 extends below the metatarsal head 12 and is interposed between the metatarsal head 12 and one or more sesamoid bones 30, with an opposite end of the malleable retractor 50 positioned downward to retract soft tissues away from the device 1.

Step 6A is performed after step 6 and prior to step 7.

Other embodiments not specifically set forth herein are also within the scope of the following claims.

I claim:

1. An osteotomy guide and retraction device for use on a metatarsal having a head and a neck, comprising a clamp, said clamp comprising a handle assembly, having a first handle, a second handle, and a hinge mechanism, said first and second handles suitably adapted to be held and manipulated by a human hand and to articulate about the hinge mechanism, a primary jaw, said primary jaw depending from said first handle with the hinge mechanism interposed between said primary jaw and said first handle, a secondary jaw, said secondary jaw depending from said second handle with the hinge mechanism interposed between said secondary jaw and said second handle, wherein said secondary jaw is suitably adapted to retract an extensor tendon by displacing said tendon away from the head of the metatarsal and retaining said tendon in a retracted position while the device is engaged upon the neck of the metatarsal, and a locking assembly integrated with the handle assembly and suitably adapted to hold the primary and secondary jaws in a fixed position relative to each other, whereby manipulation of said first and second handles causes said primary and secondary jaws to move towards and away from each other; a guide plate, said guide plate being substantially planar and having an outer surface, an inner surface, and a thickness, wherein the guide plate is integrated with and depends from the primary jaw, said guide plate comprising two or more guide slots, with each said guide slot being substantially linear and formed into and passing completely through the thickness of said guide plate, and with each said guide slot having a length and width, wherein the width of each said guide slot is slightly wider than a thickness of a cutting blade so as to accommodate the passing of said cutting blade through said guide slot, and the length of each said guide slot is suitably adapted to permit said cutting blade to make an appropriate length incision into and through the head of the metatarsal, wherein the said two or more guide slots are suitably oriented on said guide plate with respect to each other to permit said cutting blade to make appropriately positioned incisions into and through the head of the metatarsal, wherein the guide plate comprises four guide slots, with the four guide slots denoted A, B, C, and D, respectively, with all four guide slots intersecting with each other at acute angles, with guide slot A forming a substantially 60 degree angle with guide slot D, guide slot B forming a substantially 40 degree angle with guide slot C, guide slot A forming a substantially 50 degree angle with guide slot C, guide slot B forming a substantially 50 degree angle with guide slot D, guide slot A forming a substantially 10 degree angle with guide slot B, and guide slot C forming a substantially 10 degree angle with guide slot D, and with guide slots B and C being longer than guide slots A and D, thereby facilitating the making of multiply configured chevron cuts into and through the head of the metatarsal; a primary metatarsal engagement device, said primary metatarsal engagement device located on the inner surface of the guide plate, said primary metatarsal engagement device having an open, substantially concave configuration forming an engagement surface suitably adapted to snugly fit over and against a portion of the neck of the metatarsal, whereby the primary metatarsal engagement device when engaged with the neck of the metatarsal is suitably adapted to correctly position the guide plate with respect to the head of the metatarsal; and a secondary metatarsal engagement device, said secondary metatarsal engagement device depending from the secondary jaw, with said secondary metatarsal engagement device having an engagement surface suitably adapted to engage the neck of the metatarsal, whereby the secondary metatarsal engagement device when engaged with the neck of the metatarsal is suitably adapted to provide counter pressure to the primary metatarsal engagement device.

2. The device of claim 1 wherein at least one guide slot is formed into and passes completely through the primary metatarsal engagement device.

3. The device of claim 1 wherein the primary metatarsal engagement device is integrated with the guide plate.

4. The device of claim 3 wherein the primary metatarsal engagement device and the guide plate are formed of a unitary piece of metal.

5. The device of claim 1 wherein the engagement surface of the primary metatarsal engagement device comprises a plurality of gripping members.

6. The device of claim 1 wherein the engagement surface of the secondary metatarsal engagement device comprises a plurality of gripping members.

7. The device of claim 1 wherein the engagement surface of the secondary metatarsal engagement device is substantially planar.

8. The device of claim 1 wherein the secondary metatarsal engagement device has an open, substantially concave configuration suitably adapted to fit over the neck of the metatarsal.

9. The device of claim 1 wherein the engagement surface of the secondary metatarsal engagement device is oriented at an angle to the inner surface of the guide plate to accommodate the anatomy of the head of the metatarsal.

10. The device of claim 1 wherein the guide plate comprises one or more bone engagement members, with each said bone engagement member depending substantially perpendicularly from the inner surface of the guide plate, whereby each said bone engagement member is suitably adapted to engage with the metatarsal thereby assisting in securing the device to the metatarsal so that the guide plate can be correctly positioned with respect to the head of the metatarsal.

11. The device of claim 1 wherein the guide plate, the primary metatarsal engagement device, the secondary metatarsal engagement device, and the clamp are constructed of surgical stainless steel.

12. The device of claim 1 wherein the guide plate further comprises a retractor slot suitably adapted to accommodate a malleable retractor having a thickness and a width,
    said retractor slot being substantially linear and formed into and passing completely through the thickness of the guide plate,
    with said retractor slot having a length and width, wherein the width of said retractor slot is slightly wider than the thickness of said malleable retractor and the length of said retractor slot is slightly longer than the width of said malleable retractor so as to accommodate the passing of said malleable retractor through said retractor slot such that at least a portion of said malleable retractor extends below the head of the metatarsal.

13. A method for performing a bunionectomy on a metatarsal bone having a head and a neck using the device of claim 12, said method comprising the following steps:
    1. preparing a patient for surgery using standard technique;
    2. exposing the head of the metatarsal and the neck of the metatarsal medially, dorsally, and laterally, using standard technique;
    3. performing an exostectomy of the head of the metatarsal using standard technique;
    4. retracting the extensor tendon away from the site of the exostectomy;
    5. positioning the device of claim 12 onto the exposed neck of the metatarsal and against the head of the metatarsal by engaging the primary metatarsal engagement device with the neck of the metatarsal, engaging the secondary metatarsal engagement device with the neck of the metatarsal opposite the primary metatarsal engagement device, and locking the device into position;
    6. positioning the extensor tendon against the secondary jaw of the device such that the tendon is retracted by the secondary jaw, wherein the secondary jaw is interposed between the tendon and the metatarsal;
    7. making two or more incisions into and through the head of the metatarsal with a saw blade, by inserting the saw blade into and through two or more guide slots of the device of claim 12 and continuing to move the saw blade into and through the head of the metatarsal;
    8. removing the device from the metatarsal;
    9. manipulating the metatarsal into the desired position using standard technique;
    10. fixating the metatarsal using standard technique; and
    11. closing the soft tissues using standard technique.

14. The method of claim 13, said method further comprising the following step:
    6A. positioning an end of a malleable retractor into and through the retractor slot of the guide plate, such that at least a portion of the malleable retractor extends below the head of the metatarsal and is interposed between the head of the metatarsal and one or more sesamoid bones, with an opposite end of the malleable retractor positioned downward to retract soft tissues away from the device;
    whereby step 6A is performed after step 6 and prior to step 7.

15. The device of claim 1
    wherein the guide plate, the primary metatarsal engagement device, the secondary metatarsal engagement device, and the clamp are constructed of surgical stainless steel;

the guide plate further comprises one or more bone engagement members, with each said bone engagement member depending substantially perpendicularly from the inner surface of the guide plate, whereby each said bone engagement member is suitably adapted to engage with the metatarsal;

the guide plate further comprising a retractor slot suitably adapted to accommodate a malleable retractor having a thickness and a width, said retractor slot being substantially linear and formed into and passing completely through the thickness of the guide plate, with said retractor slot having a length and width, wherein the width of said retractor slot is slightly wider than the thickness of said malleable retractor and the length of said retractor slot is slightly longer than the width of said malleable retractor so as to accommodate the passing of said malleable retractor through said retractor slot such that at least a portion of said malleable retractor extends below the head of the metatarsal;

the primary metatarsal engagement device is integrated with the guide plate, with the primary metatarsal engagement device and the guide plate formed of a unitary piece of metal;

the engagement surface of the primary metatarsal engagement device comprises a plurality of gripping members; and the engagement surface of secondary metatarsal engagement device is substantially planar and comprises a plurality of gripping members, and is oriented at an angle to the inner surface of the guide plate to accommodate the anatomy of the head of the metatarsal.

16. A method for performing a bunionectomy on a metatarsal bone having a head and a neck using the device of claim 15, said method comprising the following steps:
1. preparing a patient for surgery using standard technique;
2. exposing the head of the metatarsal and the neck of the metatarsal medially, dorsally, and laterally, using standard technique;
3. performing an exostectomy of the head of the metatarsal using standard technique;
4. retracting the extensor tendon away from the site of the exostectomy;
5. positioning the device of claim 15 onto the exposed neck of the metatarsal and against the head of the metatarsal by engaging the primary metatarsal engagement device with the neck of the metatarsal, engaging the secondary metatarsal engagement device with the neck of the metatarsal opposite the primary metatarsal engagement device, and locking the device into position;
6. positioning the extensor tendon against the secondary jaw of the device such that the tendon is retracted by the secondary jaw, wherein the secondary jaw is interposed between the tendon and the metatarsal;
7. making two or more incisions into and through the head of the metatarsal with a saw blade, by inserting the saw blade into and through two or more guide slots of the device of claim 15 and continuing to move the saw blade into and through the head of the metatarsal;
8. removing the device from the metatarsal;
9. manipulating the metatarsal into the desired position using standard technique;
10. fixating the metatarsal using standard technique; and
11. closing the soft tissues using standard technique.

17. The method of claim 16, said method further comprising the following step:
6A. positioning an end of a malleable retractor into and through the retractor slot of the guide plate, such that at least a portion of the malleable retractor extends below the head of the metatarsal and is interposed between the head of the metatarsal and one or more sesamoid bones, with an opposite end of the malleable retractor positioned downward to retract soft tissues away from the device;
whereby step 6A is performed after step 6 and prior to step 7.

18. A method for performing a bunionectomy on a metatarsal bone having a head and a neck using the device of claim 1, said method comprising the following steps:
1. preparing a patient for surgery using standard technique;
2. exposing the head of the metatarsal and the neck of the metatarsal medially, dorsally, and laterally, using standard technique;
3. performing an exostectomy of the head of the metatarsal using standard technique;
4. retracting the extensor tendon away from the site of the exostectomy;
5. positioning the device of claim 1 onto the exposed neck of the metatarsal and against the head of the metatarsal by engaging the primary metatarsal engagement device with the neck of the metatarsal, engaging the secondary metatarsal engagement device with the neck of the metatarsal opposite the primary metatarsal engagement device, and locking the device into position;
6. positioning the extensor tendon against the secondary jaw of the device such that the tendon is retracted by the secondary jaw, wherein the secondary jaw is interposed between the tendon and the metatarsal;
7. making two or more incisions into and through the head of the metatarsal with a saw blade, by inserting the saw blade into and through the two or more guide slots of the device of claim 1 and continuing to move the saw blade into and through the head of the metatarsal;
8. removing the device from the metatarsal;
9. manipulating the metatarsal into the desired position using standard technique;
10. fixating the metatarsal using standard technique; and
11. closing the soft tissues using standard technique.

* * * * *